United States Patent [19]

Cameron et al.

[11] Patent Number: 4,822,873
[45] Date of Patent: Apr. 18, 1989

[54] CARMINOMYCINONE PRECURSES AND ANALOGUES

[75] Inventors: Donald W. Cameron; Geoffrey I. Feutrill; Peter G. Griffiths, all of Victoria, Australia

[73] Assignee: University of Melbourne

[21] Appl. No.: 758,560

[22] PCT Filed: Oct. 19, 1984

[86] PCT No.: PCT/AU84/00214
§ 371 Date: Jun. 18, 1985
§ 102(e) Date: Jun. 18, 1985

[87] PCT Pub. No.: WO85/01726
PCT Pub. Date: Apr. 25, 1985

[51] Int. Cl.[4] .................. C07H 15/24; C07C 49/66
[52] U.S. Cl. .................. 536/6.4; 260/365
[58] Field of Search ............ 536/6.4; 260/365; 514/34

[56] References Cited
FOREIGN PATENT DOCUMENTS 0124736 7/1903 Japan .
0110536 7/1983 Japan .
1599519 10/1981 United Kingdom .............. 549/15

Primary Examiner—Johnnie R. Brown
Assistant Examiner—Elli Peselev

[57] ABSTRACT

A compound of formula II and tautomeric forms thereof wherein:

$R_1-R_4$ are H, alkyl, aryl, alkaryl, halogen, hydroxy, alkoxy, aryloxy, aralkoxy, acyloxy, amino or alkylamino:

$R_8$ has the same meaning as given to $R_1-R_4$ or may be glycosyloxy;

$R_9$ and $R_{12}$ have the same meaning as given to $R_1-R_4$ and alternatively may be alkoxycarbonyl, aryloxycarbonyl or carboxy;

one of $R_x$ or $R_b$ is hydroxy and the other is H, hal, alkoxy, aryloxy or acyloxy;

$R_{10}$ and $R_{11}$ taken together are oxo or ethylenedioxy (provided that if $R_1$ and $R_{11}$ taken together are ethylenedioxy then if $R_4$ is hydrogen or methoxy, $R_b$ is not hydrogen or acetoxy); or $R_{10}$ is hydroxy; and

$R_{11}$ is hydroxyalkyl or dihydroxyalkyl or $-CO-R_{15}$ where $R_{15}$ is H, alkyl, aryl, aralkyl, hydroxyalkyl.

9 Claims, 6 Drawing Sheets

FORMULA I

FORMULA III

FORMULA II

FORMULA IV

(17) $R_1$ = α-L-DAUNOSAMINYLOXY. HCl; $R_2$ = H
(18) $R_1$ = $R_2$ = H
(26) $R_1$ = α-L-DAUNOSAMINYLOXY. HCl; $R_2$ = OH (19) $R_1$ = $R_2$ = H
(20) $R_1$ = α-L-DAUNOSAMINYLOXY; $R_2$ = H      (21) $R_1$ = α-L-DAUNOSAMINYLOXY; $R_2$ = H
(22) $R_1$ = α-L-DAUNOSAMINYLOXY; $R_2$ = OH    (23) $R_1$ = α-L-DAUNOSAMINYLOXY; $R_2$ = OH

FIG. 5

Formula I

Formula III

Formula II

Formula IV

FIG. 6

CARMINOMYCINONE PRECURSES AND ANALOGUES

This invention relates to organic compounds including anthracyclines and anthracyclinones. In a specific aspect this invention relates to carminomycinone and analogues and derivatives thereof including daunomycinone and analogues and derivatives thereof, to novel organic compounds which are useful in the synthesis of carminomycinone and its analogues and derivatives, to methods of production of organic compounds which are valuable precursors in the production of carminomycinone and its derivatives and analogues and to methods of production of analogues of anthracyclines.

Reference will be made to the accompanying drawings which are structural drawings of various chemical compounds and reaction schemes.

The compounds of formula I

FORMULA I are named; according to the substituents borne, as set out below. The three glycosides are isolated and administered as salts, usually hydrochlorides. All amino compounds referred to throughout this specification and claims are considered to include salts as well as free bases.

|  | R' | R'' | R''' |
|---|---|---|---|
| Daunomycin | $CH_3$ | H | alpha-L-daunosaminyl |
| Adriamycin | $CH_3$ | OH | alpha-L-daunosaminyl |
| Carminomycin | H | H | alpha-L-daunosaminyl |
| Daunomycinone | $CH_3$ | H | H |
| Adriamycinone | $CH_3$ | OH | H |
| Carminomycinone | H | H | H |

Modified compounds with different glycosidic residues including oligosaccharides, and with different aglycones are known, in particular those where the glycosidic sugar is 4'-deoxy-, 4'-epi-, or N-trifluoroacetyl-daunosamine and/or where the aglycone lacks the oxy substituent at position 4 or 11.

At least the compounds daunomycin and adriamycin are therapeutically useful. The other compounds at least have utility as intermediates in the production of pharmaceuticals.

The present invention provides compounds of formula III

FORMULA III and tautomeric forms thereof wherein:

$R_1$–$R_4$ are H, alkyl, aryl, alkaryl, halogen, hydroxy, alkoxy, aryloxy, aralkoxy, acyloxy, amino or alkylamino; $R_a$ is H, halogen, alkoxy, aryloxy or acyloxy; and $R_b$ is H, halogen, alkoxy, aryloxy or acyloxy.

Provided that if $R_1$–$R_4$ and $R_a$ are all, H, $R_b$ is not H or chloro. and provided that if $R_1$–$R_4$ are all H and $R_a$ is chloro or bromo $R_b$ is not chloro.

Preferred compounds of formula III are those wherein:

(a) not all of $R_1$–$R_4$ are H;
(b) $R_4$ is hydroxy, alkoxy, aralkoxy or acyloxy;
(c) $R_a$ is H, Br, Cl; and
(d) $R_b$ is H, Br, Cl, methoxy, acyloxy.

The present invention also provides compounds of formula IV

FORMULA IV and tautomeric forms thereof wherein:

$R_1$ is H, alkyl, aralkyl or acyl;
$R_2$ is H, halogen, alkoxy, aryloxy or acyloxy; or
$R_3$ is H, halogen, alkoxy, aryloxy or acyloxy.

Preferred compounds of formula IV are those wherein:

(a) $R_1$ is H or methyl;
(b) $R_2$ is H, Br or Cl; or
(c) $R_3$ is H, Br, Cl.

The present invention also provides compounds of formula II

FORMULA II and tautomeric forms thereof wherein: $R_1$–$R_4$ have the meaning given above;

$R_8$ has the same meaning as given to $R_1$–$R_4$ or may be glycosyloxy;

$R_9$ and $R_{12}$ have the same meaning as given to $R_1$–$R_4$ and alternatively may be alkoxycarbonyl, aryloxycarbonyl or carboxy;

one of $R_x$ or $R_b$ is hydroxy and the other is H, hal, alkoxy, aryloxy or acyloxy;

$R_{10}$ and $R_{11}$ taken together are oxo or ethylenedioxy (provided that if $R_{10}$ and $R_{11}$ taken together are ethylenedioxy then if $R_4$ is hydrogen or methoxy, $R_b$ is not hydrogen or acetoxy); or $R_{10}$ is hydroxy; and $R_{11}$ is hydroxyalkyl or dihydroxyalkyl or —CO—$R_{15}$ where $R_{15}$ is H, alkyl, aryl, aralkyl, hydroxyalkyl.

Preferred compounds of formula II are those wherein:

(a) not all of $R_1$–$R_4$ is H;
(b) $R_4$ is hydroxy, alkoxy, aralkoxy or acyloxy;
(c) (I) $R_x$ is hydroxy; $R_b$ is H, Br, Cl, methoxy;
  (i) $R_8$, $R_9$ and $R_{12}$ are H and $R_{10}$ and $R_{11}$ taken together are oxo;

or (ii) $R_8$ is hydroxy or glycosyloxy; and $R_9$ and $R_{12}$ are H; and $R_{10}$ is hydroxy; and $R_{11}$ is hydroxyalkyl, dihydroxyalkyl or $R_{11}$ is —CO—$R_{15}$ where $R_{15}$ is H, alkyl, aryl, aralkyl, hydroxyalkyl; or (c)(II) $R_x$ is H; $R_b$ is hydroxy; $R_8$ is H, hydroxy, glycosyloxy; $R_9$ and $R_{12}$ are H and $R_{10}$ is hydroxy; and $R_{11}$ is —CO—$R_{15}$ where $R_{15}$ is H, alkyl, aryl, aralkyl, hydroxyalkyl; or $R_{11}$ is hydroxyalkyl, dihydroxyalkyl.

The present invention also provides compounds of formula II and tautomeric forms thereof wherein:

(i) $R_1$–$R_3$ are H; $R_4$ and $R_x$ taken together are —OSO$_2$O—; $R_b$ is hydroxy, alkoxy, aralkoxy or acyloxy; $R_8$–$R_{15}$ are as defined above. or (ii) $R_1$ and $R_b$ taken together are —OSO$_2$O—R$_2$–$R_4$ are H $R_x$ is hydroxy, alkoxy, aralkoxy or acyloxy; $R_8$–$R_{15}$ are as defined above.

The present invention also provides the novel compounds 3, 4, 5, 6, 7, 9, 10, 11, 12, 13, 14, 15, 19, 20, 21, 22, 23, 24 and 25 of the Reaction Schemes I, II, III or V depicted hereinbelow. These novel compounds enumerated hereinabove may be substituted, if desired and where possible, with any one or more of $R_1$–$R_{15}$, $R_x$, $R_a$ or $R_b$ as defined above.

The present invention provides a method of obtaining a precursor of carminomycinone or of daunomycinone or their analogues or derivatives comprising reacting a compound of formula III depicted herein-above with a substituted butadiene under conditions forming the A ring of a compound of formula II depicted herein-above and converting the group $R_b$ at position 10 in formula III to a hydroxy group which taken with the hydroxy group at position 9 in formula III leads to a system tautomeric with the anthracyclinone chromophore.

The present invention provides a method of obtaining a precursor of carminomycinone or its analogues or derivatives comprising reacting a compound of formula IV depicted herein-above with a substituted butadiene under conditions forming the A ring of a compound of formula II depicted herein-above and converting the group $R_1$ in formula IV to H and hydrolysing the bridging sulfate.

If necessary, a compound so obtained is further reacted to obtain a desired compound of formula II.

The present invention also provides a method of obtaining precursors of 4-deoxy carminomycinone, that is of 4-demethoxy daunomycinone, or its analogues or derivatives comprising reacting a compound of formula III depicted herein-above, where $R_4$ is H and $R_1$–$R_3$, $R_a$ and $R_b$ are as defined above, with a substituted butadiene under conditions forming the A ring of a compound of formula II depicted herein-above and converting the group $R_b$ at position 10 in formula III to a hydroxy group which taken with the hydroxy group at position 9 in formula III leads to a system tautomeric with the anthracyclinone chromophore.

The present invention also provides a method of obtaining precursors of 12-deoxy carminomycinone or of 12-deoxy daunomycinone or their analogues or derivatives comprising reacting a compound of formula III with a substituted butadiene under conditions forming the A ring of a compound of formula II and, where $R_b$ is not already H, converting it to H.

The reaction with the substituted butadiene can be improved if there is a halogen atom, preferably bromine or chlorine atom, at the 2-position of the compounds of formula III or IV depicted herein-above.

Butadienes of particular interest as reagents are those bearing one or more of a 1-$R_{12}$-substituent, a 2-trialkylsilyloxy- or 2-alkoxy- or 2-hydroxyalkyl- or 2-oxoalkyl-, or 2-hydroxyoxoalkyl- or 2-dihydroxyalkylsubstituent, a 3-$R_9$-substituent, and a 4-$R_8$-substituent.

The present invention also provides a method of obtaining 5-deoxy daunomycin or 5-deoxy adriamycin or their analogues or derivatives comprising either reduction of a compound of formula I depicted herein-above or tautomeric forms thereof, where $R_1$ is not H, or reduction of a compound of formula II depicted herein-above or tautomeric forms thereof, where $R_4$ is not OH, in either case to give a compound of formula II where $R_x$ is H.

Figure 1:
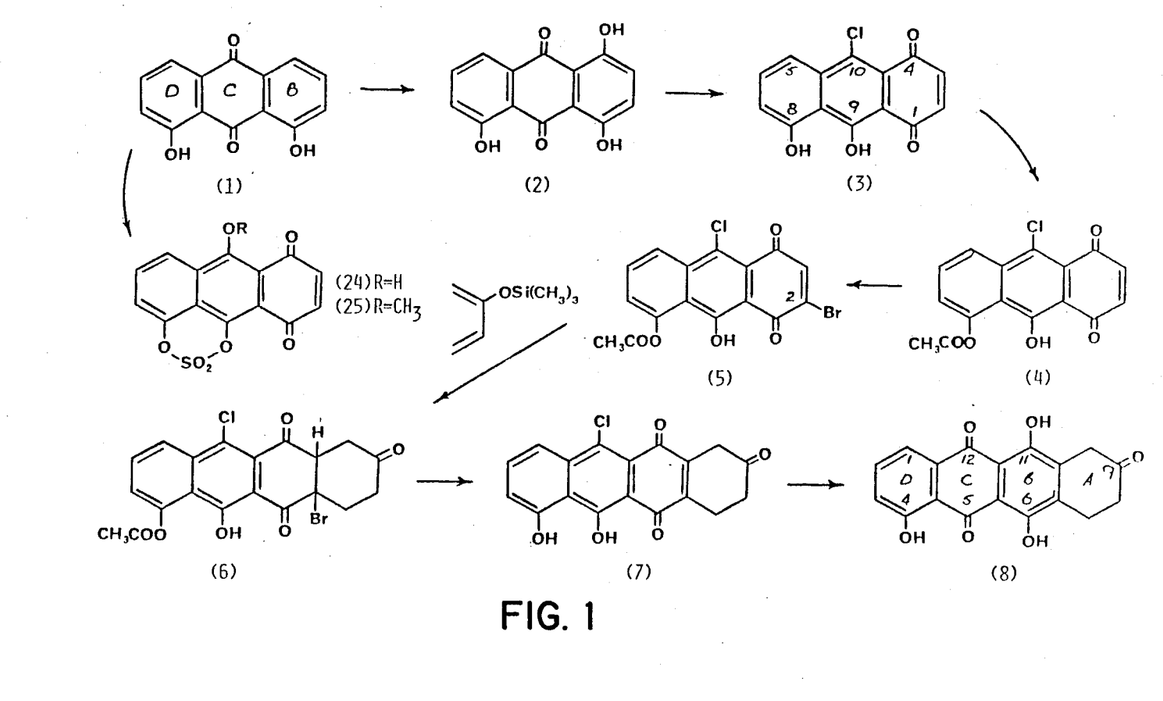

REACTION SCHEME I.

The compound 1 in scheme I which is used as a starting material is 1,8-dihydroxy-9,10-anthraquinone (chrysazin) and is available as a relatively cheap dyestuff intermediate. The step. compound 1 to compound 2 was performed in accordance with the method described in BIOS Report 1484, P.22. Omitting the hydrolytic work-up from this procedure led to compound 24, methylation of which gave compound 25.

The conversion compound 2 to compound 3 was effected in the presence of thionyl chloride and achieved, in the particular instance, three important requirements (a)–(c).

(a) The 9,10-anthraquinone compound 2 which is unsuitable for further reaction in its own right, is converted into a reactive 1,4-anthraquinone. Suitable reactivity of the latter compound results from exposure of the unsubstituted 2,3-double bond of the quinonoid system.

(b) The 1,4-anthraquinone compound 3 has the possibility of reacting regioselectively, that is with predictable discrimination between positions 2 and 3. This is because the carbonyl groups 1 and 4 which control such processes are themselves clearly differentiated, being respectively adjacent to a hydroxy and to a chloro substituent.

(c) The conversion of compound 2 into compound 3 is itself regiospecific. The potentially competitive process leading to the unwanted isomeric compound was not observed at all.

The operation compound 2 to compound 3 thus resolves a fundamental problem towards formulating a regiospecific synthesis of anthracyclines, namely of being able to use a substituent on one side of the molecule (the hydroxy group of ring D) to discriminate between reactive centres remotely located on the other side of the molecule (positions 2 and 3 of compound 3).

In the conversion compound 3 to compound 4 the more exposed of the two hydroxy groups of (3) readily undergoes selective protection to give the monoacetate (4). None of the unwanted isomeric monoacetate at the 9-position was observed.

Retention of a free hydroxy group at position 9, as in compound 4 was necessary for directive purposes in the subsequent step, conversion to the 2-bromo derivative compound 5. None of the unwanted isomeric 3-bromo derivative was observed in this step. (The 2-chloro derivative analogous to (5) has also been obtained and it shows similar chemical behaviour).

The bromo derivative compound 5 is activated towards regiospecific cycloaddition of 2-trimethylsilyloxybutadiene, a readily accessible reagent which is commercially available. On being heated smooth conversion occurs to the cycloadduct compound 6.

Treatment of the cycloadduct compound 6 then effected deacetylation and 1,2-elimination of hydrogen bromide to give the 1,4-quinone compound 7. The latter product on being treated with acid affords the tetracyclic 5,12-quinone compound 8, the desired compound in the synthesis.

The conversion compound 7 to compound 8 is an important step in the sequence, permitting hydrolytic removal of the chloro group under conditions sufficiently mild so as not to cause aromatization of ring A. This step provides the necessary complement to the step of compound 2 to compound 3 described above. Having introduced controlled discrimination into the system in the form of the chloro substituent specifically placed at position 10 of compound 3, the synthesis requires its replacement by an oxygen substituent once its function has been achieved, i.e., once an A-ring having the correct orientation has been formed. This requirement is accomplished in the conversion of compound 7 to compound 8.

In considering the sequence (5) to (6) to (7) to (8), whilst it was possible to isolate the two intermediates compounds 6 and 7 if required, it is more efficient to carry out the entire process (5) to (8) as a one-pot operation. The yield was calculated accordingly.

The tetracyclic ketone compound 8 as obtained herein was identical with an authentic sample derived by chemical degradation of natural daunomycin.

It is to be noted that the four steps (2) to (3), (3) to (4), (4) to (5), and (5) to (8), where regiochemical considerations are critical, all proceeded regiospecifically within the limits of detection.

Compound 8 can be converted into (±)-daunomycinone by Kende's method and can also be converted into (±)carminomycinone (U.S. Pat. Nos. 4,021,457 and 4,070,382). Daunomycinone can be converted into adriamycinone (U.S. Pat. No. 4,012,448). Glycosylation of these racemic anthracyclinones with appropriate derivatives of L-daunosamine (itself chemically synthesisable in enantiomeric form and commercially available) affords the natural enantiomeric anthracyclines.

In summary the conversion (1) to (8) involves five operations and proceeds in a yield of 24% overall.

Figure 2:
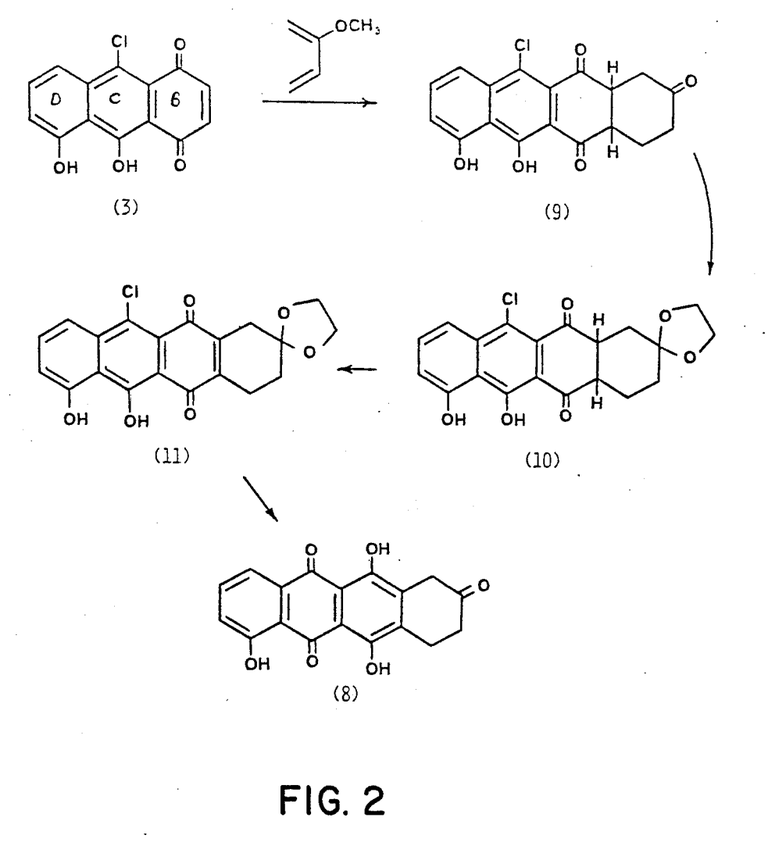

REACTION SCHEME II.

SCHEME II

A modified synthesis of compound 8 is shown in Reaction Scheme II.

It differs from the synthesis in Scheme I in effecting cycloaddition to the 1,4-anthraquinone compound 3 directly, so as to give the new cycloadduct compound 9. This avoided the acetylation and bromination steps used in Example I but it suffers from the disadvantage that cycloaddition to compound 3 requires more severe conditions than to the bromo acetate compound 5. Cycloaddition to compound 3 might conceivably have proceeded less regiospecifically than to compound 5, since the bromo substitutent in such systems generally provides a powerful directive influence; however none of the unwanted orientation was observed.

The cycloadduct compound 9 is at the oxidation level of a dihydro quinone. Oxidation to the corresponding quinone system is achieved by first protecting the isolated keto group in compound 9 as its acetal compound 10, so as to prevent aromatization of the A-ring during oxidation. Base-catalysed aerial oxidation of compound 10 then gives the protected quinone compound 11, treatment of which with trifluoroacetic acid as in the last stage of Scheme I again gives the tetracyclic ketone compound 8.

REACTION SCHEME III

SCHEME III

-continued

Figure 3:
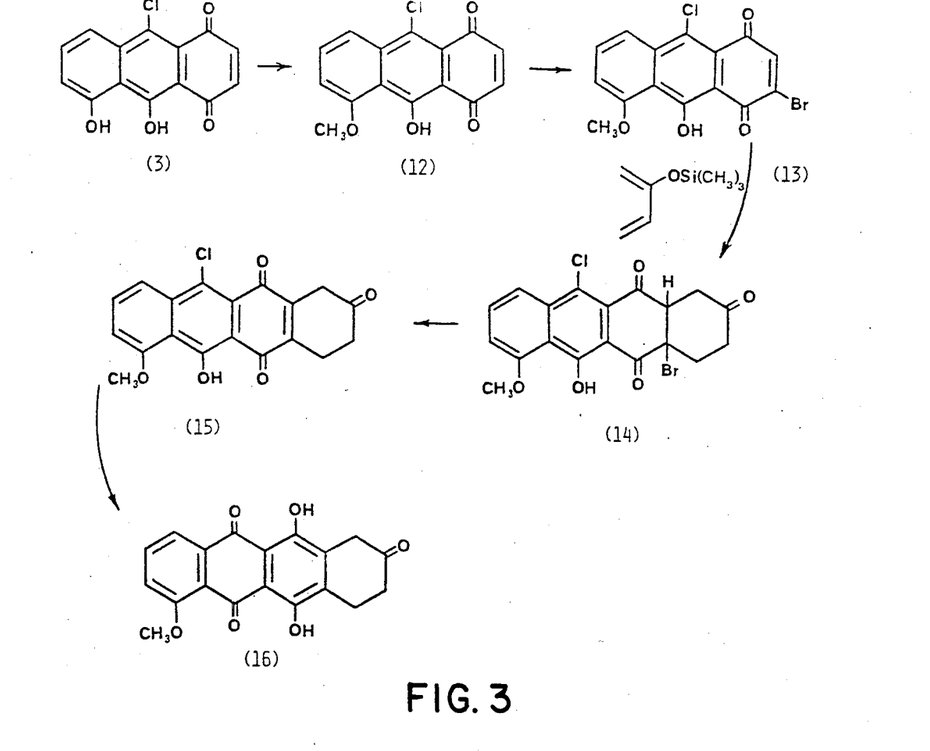

A modified synthesis is shown in Reaction Scheme III and involves methylation of compound 3 under the defined conditions which occurred regiospecifically to give the monomethyl ether compound 12, substantially exclusively. In the following stages of the sequence via compound 13 to compound 14 to compound 15 to compound 16 the monomethyl ether compound 12 went through an analogous procedure to that applied to the monoacetate compound 4 in Scheme I. The tetracyclic methoxy ketone compound 16 resulting from this sequence can be converted to (±)-daunomycinone (U.S. Pat. Nos. 4,021,457 and 4,070,382).

There are two advantages of this pathway relative to those of Schemes I and II. First the methoxy group at position 4, present in the natural anthracyclines is incorporated efficiently early in the synthesis rather than at a later poorer-yielding stage. Second the overall synthesis can be achieved in one less step and with much higher efficiency. Thus the overall yield of (±)daunomycinone from 1,8-dihydroxyanthraquinone by the pathway of Scheme III is 4.2% in eight operations. This compares with a yield of 1.8% in nine operations by Scheme I.

Figure 4:
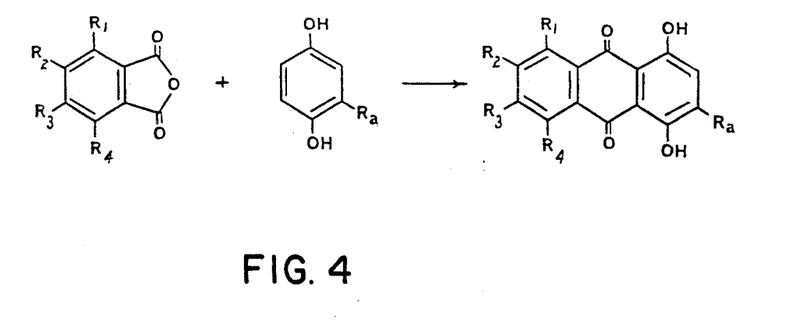

REACTION SCHEME IV.

SCHEME IV

Suitable starting materials analogous to compound 2 were made as shown in Reaction Scheme IV.

Figure 5:
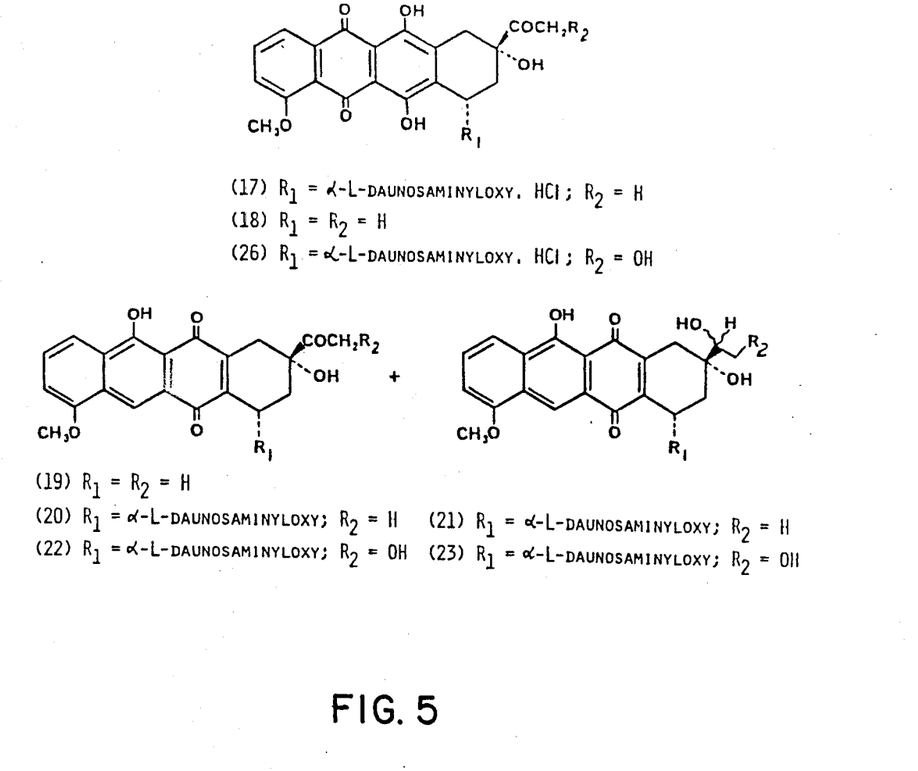
Figure 6:
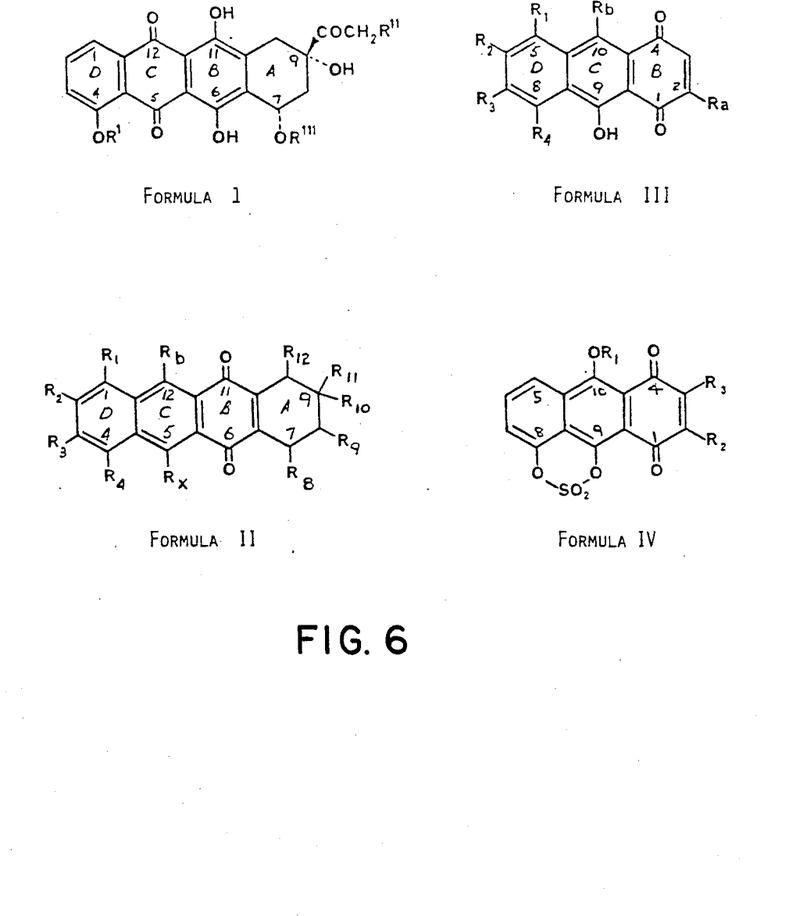

REACTION SCHEME V.

(17) $R_1$ = α-L-DAUNSAMINYLOXY, HCl; $R_2$ = H
(18) $R_1$ = $R_2$ = H
(26) $R_1$ = α-L-DAUNOSAMINYLOXY, HCl; $R_2$ = OH (19) $R_1$ = $R_2$ = H
(20) $R_1$ = α-L-DAUNOSAMINYLOXY; $R_2$ = H
(21) $R_1$ = α-L-DAUNOSAMINYLOXY; $R_2$ = H
(22) $R_1$ = α-L-DAUNOSAMINYLOXY; $R_2$ = OH
(23) $R_1$ = α-L-DAUNOSAMINYLOXY; $R_2$ = OH

Selective reduction of daunomycin 17 under mildly acidic conditions leads to the 5-deoxy compound 20 in yield of 57% and to the 5-deoxy-13-dihydro compound 21 in yield of 25%. Minor modification of this reaction leads to compound 21 in yield of 71% as the sole glycosidic product. Similar reduction of adriamycin 26 gives the 5-deoxy compound 22 in yield of 38% and the 5-deoxy-13-dihydro compound 23 in yield of 17%.

Extended reduction of 17 gives the 5,7-bisdeoxy compound 19 in yield of 88%. Compound 19 is also obtained by reduction of the known 7-deoxy daunomycinone 18.

The present invention will be further illustrated with the aid of the following examples.

EXAMPLE I

Preparation of 1,4,5-Trihydroxy-9,10-anthracenedione (compound 2) and of the Cyclic Sulfate (compound 25).

1,8-Dihydroxy-9,10-anthracenedione (chrysazin) (compound 1) (6.85 g) was added slowly to a stirred solution of 80% oleum (137 g) containing boric acid (3.56 g) maintained at 27° in an oil bath. The resulting purple mixture was stirred for 14 days, then carefully diluted to 83% sulfuric acid by addition to ice (56 g) contained in a very well cooled flask. The resulting blue mixture was then heated at 140° for 80 min under an air condenser. The mixture was cooled to room temperature then diluted into ice-cold water (600 ml) with stirring. The suspension was heated to 90° on a steam bath, cooled and filtered through pulped filter paper on a Buchner funnel. The cake was washed with distilled water (200 ml) then dried under reduced pressure, prior to exhaustive extraction with hot ethyl acetate (1000 ml). The extracts were filtered and evaporated to give a dark red solid which was recrystallized from acetic acid to give the product (compound 2) as red needles, (5.76 g, 79%).

Alternatively, the purple mixture from the foregoing reaction was added to sufficient ice to cause precipitation. Extraction with dichloromethane and preparative chromatography of the extract on silica gel 60 with chloroform as eluant gave the product (compound 24). A sample of this compound (10 mg) was stirred with an excess of methyl iodide in chloroform (3 ml) in the presence of silver oxide (36 mg) for 72 h. at room temperature. The mixture was then filtered and the filtrate evaporated. The residue was chromatographed on silica gel G with chloroform as eluant to give the product (compound 25) (10 mg, 98%).

EXAMPLE 2

Preparation of 10-Chloro-8,9-dihdroxy-1,4-anthracenedione (compound 3).

1,4,5-Trihydroxy-9,10-anthracenedione (compound 2) (670 mg) was refluxed in freshly distilled thionyl chloride (7 ml) for 40 h while being protected from moisture. The excess thionyl chloride was evaporated and the residue was taken up in dichloromethane and allowed to stand overnight. The crystals which separated were filtered off and dried. The mother liquor was applied to a column of silica gel type 60 and eluted with chloroform then chloroform/acetone/acetic acid (95:5:1). The separated purple band was added to the crystals obtained above to give a combined yield of purple-black product (compound 3) (586 mg, 81%).

EXAMPLE 3

Preparation of 8-Acetoxy-10-chloro-9-hydroxy-1,4-anthracenedione (compound 4).

10-Chloro-8,9-dihydroxy-1,4-anthracenedione (compound 3) (180 mg) was dissolved with stirring in dry tetrahydrofuran (15 ml) at room temperature. Acetic anhydride (20 drops) and pyridine (15 drops) were added to the solution which was then stirred for 48 h. Acidified water was added and the suspension was extracted with dichloromethane. The combined organic layers were dried and evaporated, and the residue was column chromatographed on silica gel 60 (100 g) with chloroform/acetone mixture as the eluant. The major red band gave the product (compound 4) as a red solid (177 mg, 85%).

EXAMPLE 4

Prepartation of 8-Acetoxy-10-chloro-9-hydroxy-1,4-anthracenedione (compound 5).

8-Acetoxy-10-chloro-9-hydroxy-1,4-anthracenedione (compound 4) (52 mg) was warmed in acetic acid (2 ml) in a round bottom flask. The mixture was cooled and to this was added a solution of bromine (28 mg) in acetic acid (0.1 ml) with stirring. After 1.5 h the yellow solution was evaporated to give a dark yellow solid which was boiled with ethanol (5 ml) for 3 min on a water bath. The red mixture was cooled. diluted with water and extracted into dichloromethane. Evaporation gave a red solid which was column chromatographed on silica gel 60 with chloroform as eluant. The mobile red band was recovered to give the product (compound 5) as a red crystalline solid (64 mg, 98%).

EXAMPLE 5

Preparation of 7,10-Dihydro-4,6,11-trihydroxy-5,9,12 (8 H)-naphthacenetrione compound 8).

8-Acetoxy-2-bromo-10-chloro-9-hydroxy-1,4-anthracenedione (compound 5) (20 mg) was treated with 2-trimethylsilyloxy-1,3-butadiene (72 mg) in refluxing benzene (2.5 ml) under nitrogen for 6 h. The benzene was evaporated under reduced pressure and the residue (compound 6) was dissolved in trifluoromethanesulfonic acid (0.5 ml) at room temperature with stirring for 10 min. The blue solution was then quenched with ice water and extracted with dichloromethane. The combined organic extract was dried and evaporated to a purple solid (compound 7). This was taken up in trifluoroacetic acid (5 ml) and heated at reflux under a nitrogen atmosphere for 60 min. The orange solution was then diluted with water and extracted with dichloromethane. The dried organic layers were chromatographed on silica gel layers containing 2% oxalic acid in toluene/ethyl acetate (90:10). The orange band Rf=0.46 was recovered to give the product (compound 8) as a red solid (7.5 mg, 45%).

EXAMPLE 6

Preparation of 3,4,4a, 12a-Tetrahydro-11-chloro-6,7-dihydroxy-2,5,12(1H)-naphthacenetrione (compound 9).

10-Chloro-8,9-dihydroxy-1,4-anthracenedione (compound 3) (100 mg), 2-methoxy-1,3-butadiene (564 mg) and dry benzene (10 ml) were heated in a sealed tube for 4 h at 130°. After cooling the crude solution was preparatively chromatographed on silica gel layers containing oxalic acid (2%) with chloroform as eluant. The major yellow band was recovered to give the product (compound 9) as a yellow crystalline solid (85 mg, 68%).

EXAMPLE 7

Preparation of Ethylene Acetal of 3,4,4a,12a-Tetrahydro-11-chloro-6,7-dihydroxy-2,5,12(1H)-naphthacenetrione (compound 10).

A solution of 3,4,4a,12a-tetrahydro-11-chloro-6,7-dihydroxy-2,5,12(1H)-naphthacenetrione (compound 9) (17 mg). p-toluenesulfonic acid (4 mg) and ethylene glycol (140 mg) in dry benzene (5 ml) was boiled under reflux for 4 h with azeotropic removal of water. Recovery of the product by partitioning with chloroform and aqueous sodium bicarbonate (5%), drying of the organic phase and evaporation under reduced pressure gave the product (compound 10) which was recrystalized from dichloromethane and light petroleum as yellow needles (18 mg, 95%).

EXAMPLE 8

Preparation of Ethylene Acetal of 3,4-Dihydro-11-chloro-6,7-dihydroxy-2,5,12(1H)-naphthacenetrione (compound 11).

Oxygen was bubbled through a solution of ethylene acetal of 3,4,4a,12a-tetrahydro-11-chloro-6,7-dihydroxy-2,5,12(1H)-naphthacenetrione (compound 10) (15 mg in 5 ml 1M aqueous sodium hydroxide) and dimethylsulfoxide (20 ml) for 30 min. The purple solution was then acidified with aqueous acetic acid and extracted with chloroform. The combined extracts were washed with water, dried and evaporated under reduced pressure to give a residue which was chromatographed on a silica gel layer containing oxalic acid (2%) with toluene/ethyl acetate (ratio 7:3) as eluant. The major purple band was recovered to give the product (compound 11) as black needles from dichloromethane/light petroleum (11 mg, 73%).

EXAMPLE 9

Preparation of 7,10-Dihydro-4,6,11-trihydroxy-5,9,12(8H)-naphthacenetrione- (compound 8).

A solution of ethylene acetal of 3,4-dihydro-11-chloro6,7-dihydroxy-2,5,12(1H)-naphthacenetrione (compound 11) (4 mg) in trifluoroacetic acid (2 ml) was heated at 80° under reflux for 1 h. The solution was cooled, diluted with distilled water (10 ml) and extracted with ethyl acetate. The combined organic layers were washed with distilled water, dried and evaporated to give the crude product (compound 8) which was recrystallized from ethyl acetate as brown microcrystals (2.5 mg 74%).

EXAMPLE 10

Preparation of 10-Chloro-9-hydroxy-8-methoxy-1,4anthracenedione (compound 12).

10-Chloro-8, 9-dihydroxy-1,4-anthracenedione (compound 3) (100 mg) was dissolved with stirring in dry dimethyl sulfoxide (25 ml) under a nitrogen atmosphere. Sodium hydride (80% dispersion, 28.5 mg) was added to the solution in one aliquot. The resulting dark blue solution was stirred for 5 min then methyl iodide (156 mg, 0.1 ml) was added in one lot. Stirring was continued for 10 min then another aliquot of methyl iodide (0.1 ml) was added to the mixture. After a further 5 min the dark blue solution was quenched with ice-cold phosphate buffer (pH 7) to give a red suspension which was extracted with chloroform. The combined organic extracts were dried and evaporated to a crude solid which was chromatographed on a column of silica gel 60 with chloroform as eluant. The mobile red band gave the product (compound 12) as a red solid (84 mg, 88%).

This yield was calculated after allowing for recovered starting material (10 mg).

EXAMPLE 11

Preparation of 2-Bromo-10-chloro-9-hydroxy-8-methoxy-1,4-anthracenedione (compound 13).

10-Chloro-9-hydroxy-5-methoxy-1,4-anthracenedione (compound 12) (50 mg) was dissolved in acetic acid (5 ml) to saturation by warming. The mixture was cooled to room temperature before addition of bromine (27 mg) in acetic acid (0.15 ml). The mixture was stirred for 120 min. then excess acetic acid was evaporated under reduced pressure. The crude solid dibromide was dissolved in ethanol (5 ml) containing boron trifluoride etherate (5 drops) and heated at reflux for 20 min. The resulting red-purple solution which deposited some crystals was cooled and diluted with distilled water (20 ml). After standing overnight, the precipitated red-black solid was filtered off to give the product (compound 13) (58 mg, 91%).

EXAMPLE 12

Preparation of 7,10-Dihydro-6,11-dihydroxy-4-methoxy-5,9,12(8H)-naphthacenetrione (compound 16).

2-Bromo-10-chloro-9-hydroxy-8-methoxy-1,4anthracenedione (compound 13) (55 mg) was dissolved in dry benzene under nitrogen at reflux. 2-Trimethylsilyloxy-1,3butadiene (212 mg) in benzene (0.5 ml) was added and the mixture was refluxed for 12.5 h altogether. Excess benzene was evaporated under reduced pressure to give a dark red solid (compound 14) which was dissolved in trifluoromethanesulfonic acid at room temperature with stirring under a nitrogen atmosphere. After 20 min. the dark blue solution was quenched with ice and extracted with dichloromethane. The combined organic extracts were dried and evaporated to dryness under reduced pressure. The residue (compound 15) was dissolved in trifluoroacetic acid (5 ml) and refluxed under nitrogen for 90 min. The dark red solution was diluted with cold distilled water and then extracted with dichloromethane. The combined organic layers were dried, evaporated and the crude, residue was preparatively chromatographed on silica gel layers containing 2% oxalic acid in toluene/ethyl acetate (80:20). The red-orange band Rf=0.23-0.35 was recovered to give the product (compound 16) as a red solid (23 mg, 45%).

Alternatively the dark red solid from the foregoing reaction was dissolved in acetic acid (11 ml) containing sodium acetate (440 mg). The mixture was stirred under nitrogen for 10 min at room temperature and was then heated at reflux for a further 5 min. Extraction with dichloromethane gave compound 15 as a red solid. This was converted to compound 16 (14 mg, 30%) as above.

EXAMPLE 13

Preparation of (9R)-9-Acetyl-9,12-dihyroxy-4-methoxy7,8,9,10-tetrahydro-6,11- naphthacenedione (compound 19).

Daunomycin hydrochloride (compound 17) (20 mg) in dry methanol (20 ml) was catalytically reduced with hydrogen gas and 5% palladium on barium sulfate (20 mg) 5.5 h at room temperature. Exposure of the mixture to the atmosphere gave a red solution which was filtered, evaporated and preparatively chromatographed on silica gel layers using chloroform/methanol (98:2) as eluant. The red band Rf 0.28–0.43 gave the product (compound 19) as a red solid (12 mg, 88%).

EXAMPLE 14

Preparation of 5-Deoxy Daunomycin (compound 20) and of 5-Deoxy -13-dihydro Daunomycin (compound 21)

A solution of daunomycin hydrochloride (compound 17) (50 mg) in dry methanol (20 ml) containing chloroacetic acid (200 mg) was shaken with hydrogen and Adams catalyst (10 mg) for 50 min at room temperature. The mixture was then filtered, the filtrate diluted with water (50 ml) and washed with dichloromethane to remove non-glycosidic materials. The aqueous residue was then brought to pH 8.5 with aqueous sodium bicarbonate. Extraction with dichloromethane and chromatography on a column of silica gel 60 with chloroform-/methanol/water (100:20:1) as eluant gave 5-deoxy daunomycin (compound 20) (26 mg, 57%) as a dark red solid. Further elution with chloroform/methanol/water (80:20:1) gave 5-deoxy-13-dihydro daunomycin (compound 21) (12 mg, 25%) as a dark red solid.

EXAMPLE 15

Preparation of 5-Deoxy-13-dihydro Daunomycin (compound 21)

A solution of daunomycin hydrochoride (compound 17) (10.4 mg) in dry methanol (6 ml) was shaken with hydrogen and Adams catalyst (8.7 mg) for 70 min at room temperature. The mixture was then, filtered, the filtrate diluted with water (10 ml) and washed with dichloromethane to remove nonglycosidic materials. The aqueous residue was brought to pH 8.5 with aqueous sodium bicarbonate. Extraction with dichloromethane gave 5-deoxy-13-dihydro daunomycin (compound 21) (6.7 mg, 71%) as a dark red solid.

EXAMPLE 16

Preparation of 5-Deoxy Adriamycin (compound 22) and of 5-Deoxy-13-dihydro Adriamycin (compound 23).

A solution of adriamycin hydrochloride (compound 26) (20 mg) in dry methanol (8 ml) containing chloroacetic acid (80 mg) was shaken with hydrogen and Adams catalyst (5 mg) for 40 min at room temperature. The mixture was filtered, the filtrate diluted with water (20 ml) and brought to pH 8.5 with aqueous sodium bicarbonate. Extraction with chloroform and chromatography on a column of silica gel 60 with chloroform-/methanol/water (80:20:1) as eluant gave 5deoxy adriamycin (compound 22) (7 mg, 38%) as a dark red solid. Further elution gave 5-deoxy-13-dihydro adriamycin (compound 23) (3 mg, 17%) as a dark red solid.

Compounds in accordance with this invention which have alkyl groups as such or as part of another radical such as alkaryl, alkoxy, aralkoxy, alkaryl, aralyl, acyloxy, alkylamino, alkoxycarbonyl, mono- or polyhydroxyalkyl include those wherein the alkyl groups are saturated or unsaturated, have from 1-20 carbon atoms, preferably 1-6 carbon atoms, and may bear such substituents as are common in the art including halogen, hydroxy, amino, imino, nitroso, carbonyl, carboxy together with such other substituents as may be desired and as are listed as radicals in IUPAC nomenclature rules. Compounds in accordance with this invention which have aryl groups as such or as part of another radical such as alkaryl, aralkyl, aryloxy, aryloxycarbonyl include those wherein the aryl moiety is a single or multi-ring aromatic system which may bear similar substituents as discussed above in respect of alkyl groups and which may contain hetero atoms such as nitrogen, oxygen or sulfur.

The claims form part of the disclosure of this specification.

Modifications and adaptations may be made to the above described without departing from the spirit and scope of this invention which includes every novel feature and combination of features disclosed herein.

The claims defining the invention are as follows:

1. A compound of the formula and tautomeric forms thereof wherein;

$R_1$–$R_4$ are independently hydrogen, $C_1$–$C_6$ alkyl, aryl, $C_7$–$C_{12}$ alkaryl, halogen, hydroxy, $C_1$–$C_6$ alkoxy, aryloxy, $C_7$–$C_{12}$ aralkoxy, acyloxy, amino or $C_1$–$C_6$ alkylamino;

$R_8$ is hydrogen, hydroxy, $C_1$–$C_6$ alkoxy, aryloxy, acyloxy, amino, $C_1$–$C_6$ alkyamino or glycosyloxy;

$R_9$ and $R_{12}$ are hydrogen, $C_1$–$C_6$ alkyl, aryl, $C_7$–$C_{12}$ alkaryl, halogen, acyloxy, $C_1$–$C_6$ alkoxycarbonyl, aryloxycarbonyl or carboxy;

one of $R_x$ and $R_b$ is hydroxy and the other is hydrogen, halogen, $C_1$–$C_6$ alkoxy, aryloxy, or acyloxy; or $R_4$ and $R_x$ or $R_1$ and $R_b$ taken together are —OSO$_2$O—;

$R_{10}$ and $R_{11}$ taken together are oxo or ethylenedioxy (provided that if $R_{10}$ and $R_{11}$ taken together are ethylenedioxy then if $R_4$ is hydrogen or methoxy, $R_b$ is not hydrogen or acetoxy); or $R_{10}$ is hydroxy; and $R_{11}$ is $C_1$–$C_6$ hydroxyalkyl or $C_1$–$C_6$ dihydroxyalkyl or —CO—$R_{15}$ where $R_{15}$ is hydrogen, $C_1$–$C_6$ alkyl, aryl, $C_7$–$C_{12}$ aralkyl or $C_1$–$C_6$ hydroxyalkyl; and wherein aryl and aryloxy groups are single ring systems which may contain hetero atoms selected from the group consisting of nitrogen oxygen and sulfur.

2. A compound in accordance with claim 1, wherein $R_{10}$ and $R_{11}$ taken together are oxo.

3. A compound in accordance with claim 1 or claim 2, wherein;

$R_4$ is hydroxy, alkoxy, aralkoxy or acyloxy;

$R_x$ is hydroxy;

$R_b$ is H, Br, Cl or methoxy; and $R_8$, $R_9$ and $R_{12}$ are H and $R_{10}$ and $R_{11}$ taken together are oxo.

4. A compound in accordance with claim 1 or claim 2, wherein;

$R_4$ is hydroxy, alkoxy, aralkoxy or acyloxy;

$R_x$ is H; $R_b$ is hydroxy; $R_8$ is H, hydroxy, glycosyloxy;

$R_9$ and $R_{12}$ are H and $R_{10}$ is hydroxy; and $R_{11}$ is hydroxyalkyl, dihydroxyalkyl, or CO-$R_{15}$, wherein $R_{15}$ is H, alkyl, aryl, aralkyl, hydroxyalkyl.

5. A compound in accordance with claim 1 or claim 2 wherein $R_1$–$R_4$ are H;

$R_8$ is alkyl, aryl, alkaryl, halogen, hydroxy, alkoxy, aryloxy, aralkoxy, acyloxy, amino, alkylamino or glycosyloxy;

$R_9$ and $R_{12}$ are independently H, alkyl, aryl, alkaryl, halogen, hydroxy, alkoxy, aryloxy, aralkoxy, acyloxy, amino, alkylamino, alkoxycarbonyl, aryloxycarbonyl or carboxy;

one of $R_x$ or $R_b$ is hydroxy and the other is H, hal, alkoxy, aryloxy or acyloxy;

$R_{10}$ and $R_{11}$ taken together are oxo or ethylenedioxy; or $R_{10}$ is hydroxy; and $R_{11}$ is hydroxyalkyl, dihydroxyalkyl or —CO—$R_{15}$ where $R_{15}$ is H, alkyl, aryl, aralkyl, hydroxyalkyl.

6. A compound according to claims 1 or 2 wherein:
$R_1$–$R_3$ are H;
$R_4$ and $R_x$ taken together are $OSO_2O$—; and
$R_b$ is hydroxy, alkoxy, aralkoxy or acyloxy.

7. A compound according to claim 1 wherein
$R_4$ is hydroxy, alkoxy, aralkoxy or acyloxy;
$R_x$ is hydroxy;
$R_b$ is hydrogen, bromine, chlorine, or methoxy;
$R_8$ is hydroxy or glycosyloxy;
$R_9$ and $R_{12}$ are hydrogen;
$R_{10}$ is hydroxy;
$R_{11}$ is hydroxyalkyl, dihydroxyalkyl or CO—$R_{15}$;
$R_{15}$ is hydrogen, alkyl, aryl, aralkyl or hydroxyalkyl.

8. A compound selected from the group consisting of [10-chloro-8,9-dihydroxy-1,4-anthracenedione, 8-acetoxy-10-chloro-9-hydroxy-1,4-anthracenedione, 8-acetoxy-2-bromo-10-chloro-9-hydroxy-1,4-anthracenedione,]3, 4,4a,12a,-tetrahydro-11-chloro-6-,6-dihydroxy-2,5,12 (1H)-naphthacenetrione, an ethylene acetal of 3,4,4a,12a-tetrahydro-11-chloro-6,7-dihydroxy-2,5,12 (1H)-naphthacenetrione, an ethylene acetal of 3,4-dihydro-11-chloro-6,7-dihydroxy-2,5,12 (1H)-naphthacenetrione, [10-chloro-9-hydroxy-8-methoxy-1,4-anthracenedione, 2-bromo-10-chloro-9-hydroxy-8-methoxy-1,4-anthracenedione,](9R)-9-acetyl-9,12-dihydroxy-4-methoxy-7, 8,9,10-tetrahydro-6,11-naphthacenedione, 5-deoxy aunomycin, 5-deoxy-13-dihydro daunomycin, 5-deoxy-adriamycin, 5-deoxy-13-hydro adramycin,

,

, or

9. The compound according to claims 1 or 2 wherein
$R_1$ and $R_b$ taken together are —$OSO_2O$—;
$R_2$–$R_4$ are H; and
$R_x$ is hydroxy, alkoxy, aralkoxy or acyloxy.

UNITED STATES PATENT AND TRADEMARK OFFICE
CERTIFICATE OF CORRECTION

PATENT NO. : 4,822,873

DATED : April 18, 1989

INVENTOR(S) : Donald W. Cameron, et al.

It is certified that error appears in the above-identified patent and that said Letters Patent is hereby corrected as shown below:

On the Title page, Section [73]: "University of Melbourne" should read as --The University of Melbourne and Anti-Cancer Council of Victoria--

Signed and Sealed this

Seventh Day of January, 1992

Attest:

HARRY F. MANBECK, JR.

Attesting Officer

Commissioner of Patents and Trademarks